United States Patent [19]

Guzowski et al.

[11] 4,266,973

[45] May 12, 1981

[54] TARNISH-RESISTANT GOLD COLOR ALLOY AND DENTAL RESTORATIONS EMPLOYING SAME

[75] Inventors: Matthew M. Guzowski, Wallingford; Stephen P. Schaffer, Bloomfield; David C. Wright, Enfield, all of Conn.

[73] Assignee: The J. M. Ney Company, Bloomfield, Conn.

[21] Appl. No.: 103,846

[22] Filed: Dec. 14, 1979

[51] Int. Cl.$^3$ .................. C22C 5/02; C22C 5/06; C22C 5/00
[52] U.S. Cl. ....................... 75/134 N; 75/134 C; 75/165
[58] Field of Search ............... 75/165, 134 N, 134 C

[56] References Cited

U.S. PATENT DOCUMENTS

| | | | |
|---|---|---|---|
| 1,580,444 | 4/1926 | Shields | |
| 1,987,452 | 1/1935 | Taylor | 75/1 |
| 2,216,495 | 10/1940 | Loebich | 75/165 |
| 2,596,454 | 5/1952 | Williams | 75/165 |
| 2,654,146 | 10/1953 | Moordian | 29/199 |
| 3,136,633 | 6/1964 | Berry | 75/165 |
| 3,424,577 | 1/1969 | Nielsen et al. | 75/134 |
| 3,572,377 | 10/1951 | O'Morrow | 32/9 |
| 3,767,391 | 10/1973 | Tuccillo et al. | 75/134 C |
| 3,819,366 | 6/1974 | Katz | 75/172 R |
| 3,925,073 | 12/1975 | Kohrn et al. | 75/173 C |
| 4,008,080 | 2/1977 | Wagner | 75/134 N |
| 4,012,228 | 3/1977 | Dudeck et al. | 75/134 C |
| 4,014,690 | 3/1977 | Dudek et al. | 75/165 |

*Primary Examiner*—L. Dewayne Rutledge
*Assistant Examiner*—Upendra Roy

[57] ABSTRACT

A tarnish-resistant gold color alloy comprises 30–50 percent by weight gold; 20–50 percent copper; 5–15 percent silver; 2–20 percent zinc; 1.5–15 percent palladium; up to 4.0 percent by weight platinum; and up to 1.0 percent by weight rhenium. The atomic ratio of copper to silver, copper to zinc and copper to palladium are respectively, 6–8:1; 2–12:1; and 5–30:1 and the weight ratios are respectively, 3.5–4.7:1; 3.0–18:1; and 1.95–11.66:1. Dental restorations comprising castings of the alloy have color values on the Hunter scale of L=80–90; a=2.5–3.5; and b=14–18. The dental restorations exhibit tarnish-resistant values of $DE_1$ less than 13 and $DE_{10}$ less than 20.

8 Claims, No Drawings

TARNISH-RESISTANT GOLD COLOR ALLOY AND DENTAL RESTORATIONS EMPLOYING SAME

BACKGROUND OF THE INVENTION

Gold color alloys are employed for many applications where aesthetic considerations are significant including dental restorations and jewelry. Moreover, gold alloys and precious metal alloys containing substantial amounts of gold are widely employed in the electrical and electronics fields where resistance to tarnish and inertness to the atmosphere are desired. However, the ever-escalating costs of gold have necessitated a search for alloys which would provide the same aesthetic and tarnish-resistant properties at substantially lower cost.

Unfortunately, although other alloys having similar gold coloration with no, or relatively low, gold content have been formulated, generally such alloys suffer from low tarnish resistance, particularly in a sulfur-containing environment. Moreover, many such alloys do not possess the requisite hardness and other physical properties for many applications where such gold color alloys are desirable.

It is an object of the present invention to provide a novel gold color alloy which exhibits a desirable gold coloration and highly advantageous resistance to tarnish.

Another object is to provide such an alloy which is relatively low in gold content and which exhibits desirable inertness for dental and other applications together with a useful balance of physical properties.

A further object is to provide dental restorations comprising castings of such an alloy, which castings exhibit desirable physical properties and aesthetically pleasing gold coloration and a high resistance to tarnish.

SUMMARY OF THE INVENTION

It has now been found that the foregoing and related objects may be readily attained in a tarnish-resistant gold color alloy of the following elements on a weight percent basis: 30–50 gold; 20–50 copper; 5–15 silver; 2–20 zinc; 1.5–15 palladium; up to 4.0 platinum; and up to 1.0 rhenium. The atomic ratio of copper to silver, copper to zinc and copper to palladium are respectively 6–8:1; 2–12:1; and 5–30:1. The weight ratios of copper to silver, copper to palladium and copper to zinc are respectively 3.5–4.7:1; 1.95–11.66:1; and 3.0–18:1.

In accordance with the preferred embodiment of the present invention, the alloy contains 0.5–1.5 percent by weight platinum as a hardener. Desirably, 0.3–0.7 percent by weight rhenium is included to effect grain refinement.

An optimum alloy composition contains 35–45 percent gold, 33–43 percent copper, 5–10 percent zinc; 2–8 percent palladium; and 7–12 percent silver. The atomic ratios of copper to silver, copper to zinc and copper to palladium are respectively 6.5–7.5:1; 4–6:1; 14–18:1.

Dental restorations comprising castings of the alloy exhibit color values on the Hunter scale (D 65) of L=80–90; a=2.5–3.5; and b=14–18. The tarnish-resistance values of the castings are $DE_1$ of less than 13 and $DE_{10}$ of less than 20.

DETAILED DESCRIPTION OF THE PREFERRED EMBODIMENTS

As indicated hereinafter, the gold color alloys of the present invention are essentially comprised of gold, copper, silver, zinc and palladium. They may contain platinum as a hardener and may desirably contain rhenium as a grain refiner. The atomic ratios of copper to silver, copper to zinc and copper to palladium must be controlled as more fully defined herein.

The gold content may vary fairly widely within the range of 30–50 percent, recognizing that it is desirable to minimize the gold content from the standpoint of cost but also desirable to maintain a high degree of inertness. However, 30 percent represents an effective minimum content to obtain the desired balance of properties, and the preferred range is 35–45 percent. Highly desirable compositions have about 38–42 percent gold.

The other principal constituent of the alloy is copper, which is present in the range of 20–50 percent by weight, and preferably 35–45 percent. Highly desirable compositions employ 37–40 percent. The copper serves to develop the desired coloration for the alloy and also functions to provide corrosion resistance.

Silver is present in the range of 5–15 percent by weight and functions to provide tarnish resistance. Preferably, it comprises 7–12 percent of the alloy and highly desirable alloys have utilized 8–10 percent.

Palladium is present in the range of 1.5–15 percent by weight and functions to raise the melting point of the alloy and to enhance the resistance to tarnishing and inertness. The preferred alloys contain palladium in the amount of 2–8 percent. Highly desirable alloys have employed palladium within the range of 3–5 percent.

Zinc is included within the range of 2–20 percent by weight and helps to develop the yellow coloration in combination with the copper. Preferred alloys contain zinc in an amount of 5–10 percent, and highly desirable alloys have utilized 6–8 percent.

Platinum is included in an amount of up to 4 percent by weight of the alloy and functions to provide hardening characteristics to the alloy to enhance its inertness. Preferred alloys contain 0.5–2.5 percent platinum.

Rhenium may be included in an amount of up to 1 percent by weight and serves as a grain refiner. When employed, it desirably comprises 0.3–0.7 percent by weight.

The several components are relatively critically interrelated in terms of their atomic ratios in order to obtain the desired balance of properties for the alloy. More specifically, the atomic ratio of copper to silver is quite critical and must be within the range of 6–8:1 (weight ratio of 3.5–4.7:1), and preferably within the range of about 6.8–7.3:1. The atomic ratio of copper to zinc is less critical and may be within the range of 2–12:1 (weight ratio of 1.95–11.66:1), but preferably within the range of 4–6:1. The atomic ratio of copper to palladium is also less critical and may be within the range of 5–30:1 (weight ratio of 3–18:1) but is preferably within the range of 14–18:1.

By utilizing the above alloy components in the amounts and within the ratios indicated, it has been found that highly desirable tarnish-resistant gold color alloys can be obtained, and these may be utilized for various applications including jewelry, dental restorations, and electrical contacts. The alloys exhibit desirable liquidus and solidus temperatures within the range of 870°–940° C. and 800°–880° C. respectively. In addition, they exhibit a highly desirable balance of physical properties.

The alloys of the present invention exhibit a highly desirable gold coloration as measured by Hunter scale value numbers using a D 65 light source simulating natural daylight. The color coordinate system is designated CIE 1976 L*a*b* which is described by P. A. Hunter in "How Does It Look to You", *Industrial Research and Development*, August, 1979, at page 69. Utilizing the color coordinate system, an L value, which is the measure of lightness and darkness, of 80–90 is obtained for the alloy. Similarly, an a value, representing red/green coloration, of 2.5–3.5 is obtained, and b value, representing yellow/blue coloration, of 14–18 is obtained. These values compare closely to high gold content gold color alloys so that a desirable substitution may be effected.

Of particular significance is the resistance to tarnish exhibited by the alloys. Tarnish may be defined as discoloration of the metal by a surface film which is produced when the alloy reacts with the surrounding environment. The level of discoloration is measured by a spectrophotometer and is reported in "difference units" (DE). DE values are calculated from the Hunter color value numbers by the difference equation:

$$DE = \sqrt{\Delta L^2 + \Delta a^2 + \Delta b^2}$$

A DE value of one is a change that is just noticeable to the human eye.

Samples are immersed in a 22–24 percent aqueous solution of ammonium sulfide heated to 60° C. and held for 1 and 10 minutes respectively. The amount of tarnish is then measured using the above-mentioned procedure.

This procedure has been described in a paper presented to the Dental Materials Group of the International Association of Dental Researchers at their meeting in New Orleans, Louisiana in February 1979, Abstract No. 975. The paper, by D. Wright and R. German, entitled "The Quantification of Color and Tarnish Resistance of Dental Alloys", will be published in the *Journal of Dental Research*, and a copy is submitted herewith.

The alloys of the present invention are found to have tarnish resistance values of $DE_1$ and $DE_{10}$ of less than 13 and less than 20, respectively.

Exemplary of the efficacy of the alloys of the present invention are the data set forth in the following examples wherein all values are by weight unless otherwise indicated.

EXAMPLE ONE

An alloy was prepared having the following nominal composition: 40.98 percent gold, 38.01 percent copper, 1.01 percent platinum; 8.98 percent silver, 7.14 percent zinc and 8.87 percent palladium. The alloy has a copper to silver atomic ratio of 7.2, a copper to zinc atomic ratio of 5 and a copper to palladium atomic ratio of 15. The color index values of the alloy are determined as L=86.82, a=3.29 and b=14.24. Specimens are immersed in an ammonium sulfide solution and the following tarnish-resistant values are observed: $DE_1 = 6.31$ and $DE_{10} = 9.56$.

Specimens are subjected to physical testing and the following properties of the alloy as cast are determined: ultimate yield strength—69,000 p.s.i.; offset yield—35,000 p.s.i.; tensile elongation—46%; modulus of elasticity—16,000,000 p.s.i. The Vickers hardness of the alloy is determined to be 128 and its density is determined at 11.42 g/cm³. The liquidus temperature is determined at 910° C. and the solidus is determined at 840° C.

Thus, the alloy reflects a highly desirable balance of physical properties, good gold color characteristics and highly desirable tarnish resistance. Alloys of this composition are considered optimum embodiments of the present invention and are being sold commercially by Applicants' assignee.

EXAMPLE TWO

To determine the effect of varying the copper to silver atomic ratio while maintaining the copper to zinc and copper to palladium ratios constant, a series of alloy formulations were prepared as follows:

|  | 1 | 2 | 3 | 4 | 5 |
|---|---|---|---|---|---|
| Au, % | 40.43 | 40.70 | 41.08 | 41.21 | 41.32 |
| Cu, % | 35.35 | 36.42 | 37.85 | 38.36 | 38.77 |
| Pt, % | 1.00 | 1.01 | 1.02 | 1.02 | 1.02 |
| Ag, % | 12.00 | 10.31 | 8.03 | 7.23 | 6.58 |
| Zn, % | 7.27 | 7.49 | 7.79 | 7.89 | 7.97 |
| Pd, % | 3.94 | 4.07 | 4.23 | 4.29 | 4.33 |
| Cu/Ag ratio | 5. | 6. | 8. | 9. | 10. |
| Cu/Zn ratio | 5. | 5. | 5. | 5. | 5. |
| Cu/Pd ratio | 15. | 15. | 15. | 15. | 15. |
| L | 88.81 | 88.79 | 87.50 | 86.26 | 88.18 |
| a | 2.81 | 2.76 | 2.81 | 3.14 | 2.97 |
| b | 13.64 | 13.82 | 14.03 | 13.65 | 13.21 |
| $DE_1$ | 10.17 | 8.34 | 9.60 | 11.94 | 12.73 |
| $DE_{10}$ | 13.81 | 11.17 | 11.38 | 17.12 | 17.14 |

As can be seen, the red/green color value numbers vary signficantly as the ratio is changed and the tarnish values rapidly increase as the composition deviates from the preferred copper/silver atomic ratio of 7:1 so that the extremes for a desirable ratio are reflected by the range of 6–8:1.

From the foregoing detailed specification and examples, it can be seen that the alloys of the present invention provide an aesthetically pleasing gold color despite their relatively low gold content and they exhibit desirable tarnish resistance. They also demonstrate a desirable balance of physical properties and have solidus and liguidus temperatures which permit their use with many solders used with higher gold content alloys. As such, they are useful for dental, jewelry and industrial applications where aesthetic appearance, inertness, tarnish resistance and a balance of physical properties are desired.

Having thus described the invention, we claim:

1. A tarnish-resistant gold color alloy consisting essentially of:
    A. 30–50 percent by weight gold;
    B. 20–50 percent by weight copper;
    C. 5–15 percent by weight silver;
    D. 2–20 percent by weight zinc;
    E. 1.5–15 percent by weight palladium;
    F. up to 4.0 percent by weight platinum; and
    G. up to 1.0 percent by weight rhenium;

the copper to silver atomic ratio being 6–8:1; the copper to zinc atomic ratio being 2–12:1; and the copper to palladium atomic ratio being 5–30:1; the weight ratio of copper to silver being 3.5–4.7:1; the weight ratio of copper to zinc being 3.0–18:1; and the weight ratio of copper to palladium being 1.95–11.66:1.

2. The tarnish-resistant gold color alloy in accordance with claim 1 wherein there is included 0.5–1.5 percent by weight platinum.

3. The tarnish-resistant gold color alloy in accordance with claim 1 wherein the gold comprises 35–45 percent by weight, the copper comprises 33–43 percent by weight, the zinc comprises 5–10 percent by weight, the palladium comprises 2–8 percent by weight, the silver comprises 7–12 percent by weight; and wherein the copper to silver atomic ratio is 6.5–7.5:1, the copper to zinc atomic ratio is 4–6:1; and the copper to palladium atomic ratio is 14–18:1.

4. The tarnish-resistant gold color alloy in accordance with claim 3 wherein there is included 0.5–1.5 percent by weight platinum.

5. A dental restoration comprising a casting of an alloy consisting essentially of:
   A. 30–50 percent by weight gold;
   B. 20–50 percent by weight copper;
   C. 5–15 percent by weight silver;
   D. 2–20 percent by weight zinc;
   E. 1.5–15 percent by weight palladium;
   F. up to 4.0 percent by weight platinum; and
   G. up to 1.0 percent by weight rhenium;
the copper to silver atomic ratio being 6–8:1; the copper to zinc atomic ratio being 2–12:1; and the copper to palladium atomic ratio being 5–30:1; the weight ratio of copper to silver being 3.5–4.7:1; the weight ratio of copper to zinc being 3.0–18:1; and the weight ratio of copper to palladium being 1.95–11.66:1; said casting having color values on the Hunter scale (D 65) of $L = 80-90$; $a = 2.5-3.5$; $b = 14-18$; and tarnish-resistant values of $DE_1$ less than 13 and $DE_{10}$ less than 20.

6. The dental restoration of claim 5 wherein there is included 0.5–1.5 percent by weight platinum.

7. The dental restoration of claim 5 wherein the gold comprises 35–45 percent by weight, the copper comprises 33–43 percent by weight, the zinc comprises 5–10 percent by weight, the palladium comprises 2–8 percent by weight, the silver comprises 7–12 percent by weight; and wherein the copper to silver atomic ratio is 6.5–7.5:1, the copper to zinc atomic ratio is 4–6:1; and the copper to palladium atomic ratio is 14–18:1; and wherein said alloy contains 0.5–1.5 percent by weight of a hardener consisting of platinum.

8. A tarnish-resistant gold color alloy consisting essentially of:
   A. 30–50 percent by weight gold;
   B. 20–50 percent by weight copper;
   C. 5–15 percent by weight silver;
   D. 2–20 percent by weight zinc;
   E. 1.5–15 percent by weight palladium;
   F. up to 4.0 percent by weight platinum; and
   G. 0.03–0.7 percent by weight rhenium;
the copper to silver atomic ratio being 6–8:1; the copper to zinc atomic ratio being 2–12:1; and the copper to palladium atomic ratio being 5–30:1; the weight ratio of copper to silver being 3.5–4.7:1; the weight ratio of copper to zinc being 3.0–18:1; and the weight ratio of copper to palladium being 1.95–11.66:1.

* * * * *